United States Patent [19]

Suzuki

[11] Patent Number: 5,015,429
[45] Date of Patent: May 14, 1991

[54] METHOD FOR MOLDING A FOOT SHAPE

[76] Inventor: Kazutoyo Suzuki, 43-6, Higashiogu 6-chome, Arakawa-ku, Tokyo, Japan

[21] Appl. No.: 434,464

[22] Filed: Nov. 13, 1989

Related U.S. Application Data

[62] Division of Ser. No. 178,040, Apr. 5, 1988, Pat. No. 4,932,852.

[30] Foreign Application Priority Data

Apr. 6, 1987 [JP] Japan .................................. 62-84430

[51] Int. Cl.$^5$ ............................................ B29C 51/20
[52] U.S. Cl. .................... 264/138; 264/223; 264/322; 264/293
[58] Field of Search ........... 425/2, 385, 515, DIG. 32; 264/222, 223, DIG. 30, 138, 322, 293, DIG. 66; 52/DIG. 13; 249/155

[56] References Cited

U.S. PATENT DOCUMENTS

| | | | |
|---|---|---|---|
| 2,216,533 | 10/1940 | Kaplan | 425/2 |
| 2,410,888 | 11/1946 | Lucy | 249/155 |
| 2,955,326 | 10/1960 | Murray | 264/DIG. 30 |
| 3,932,105 | 1/1976 | Knoell | 425/515 |
| 4,139,337 | 2/1979 | David et al. | 425/2 |
| 4,306,856 | 12/1981 | Arippol | 264/322 |
| 4,470,782 | 9/1984 | Zimmerman, Jr. et al. | 425/2 |
| 4,521,171 | 6/1985 | Noonan, Jr. | 425/2 |
| 4,548,563 | 10/1985 | Aigrefeuille | 425/2 |
| 4,747,989 | 5/1988 | Peterson | 425/2 |

FOREIGN PATENT DOCUMENTS

| | | | |
|---|---|---|---|
| 596762 | 4/1934 | Fed. Rep. of Germany . | |
| 84/02304 | 6/1984 | PCT Int'l Appl. . | |
| 558888 | 2/1975 | Switzerland | 52/DIG. 13 |
| 1425312 | 2/1976 | United Kingdom | 249/155 |
| 1475405 | 6/1977 | United Kingdom | 264/223 |

Primary Examiner—Jeffery Thurlow
Assistant Examiner—Mathieu Vargot
Attorney, Agent, or Firm—Spencer & Frank

[57] ABSTRACT

A method of making a foot-shaped layer, such as an insole member of a shoe using an apparatus which includes a top plate having an opening of a predetermined area and mutually adjacent bar-like measuring elements frictionally supported in an individually vertically movable manner within the opening. A sheet of thermoplastic is heated to a plasticized state and placed on the opening so as to cover the upper end surfaces of the measuring elements so that upon stepping on the sheet with a foot, the film and measuring elements thereunder move downward by amounts corresponding to the shape of the foot so that the film is molded to the shape of the foot. The molded film is then cooled and cut along the outline of the foot to obtain a layer which may be used to define the shape of an insole member.

5 Claims, 3 Drawing Sheets

METHOD FOR MOLDING A FOOT SHAPE

This is a division of application Ser. No. 178,040, filed Apr. 5th, 1988, now U.S. Pat. No. 4,932,852.

BACKGROUND OF THE INVENTION

The present invention relates to a method and an apparatus for easily and precisely molding the shape of the bottom portion of a foot which will form a basis of a last to be used in making a shoe.

In order to make a shoe that fits ones foot, it is desirable to use a last which has a shape which molds substantially perfectly with the foot. Therefore, shoes were conventionally made by measuring major parts of a foot and, based on the measurement, making a last, or choosing the most fitting one from many lasts available.

Every foot is so individually shaped that it is impossible to make a precise last by merely measuring the major parts of the foot, although the last may very well correspond to the foot in the dimensions of such major parts. Prior shoes made in this way have not been completely comfortable and there has, therefore, been a demand for some measures for making shoes that are more comfortable to wear.

To relieve the fatigue from wearing shoes, it is desired to make foot-fitting shoes as mentioned above. The comfortableness in wearing the shoes can be improved by laying insoles therein, but the insoles heretofore available are typically standardized flat and flexible ones that cannot provide perfect comfort.

OBJECTS AND SUMMARY OF THE INVENTION

An object of the present invention is to provide a method of easily and quickly making a mold of the shape of the bottom portion of a foot which will form the basis of a last.

Another object of the present invention is to provide an apparatus for making a mold of such a foot shape precisely, and which is simple in construction and low in cost.

Still another object of the present invention is to provide a method of very easily making an insole which can greatly improve the comfort of the shoe.

According to a first aspect of the present invention for attaining the above objects, there is provided a method of making a foot mold comprising the steps of supporting a plurality of adjacent bar-like measuring elements in an individually vertically movable condition disposed, for example, within a molding box having a top plate provided with an opening of a predetermined area; covering upper end surfaces of the measuring elements facing the opening with a thermoplastic film which is being plasticized by heating; stepping on the film and the measuring elements thereunder so as to mold the film to the shape of the bottom of the foot, and then cooling the molded film.

According to a second aspect of the invention, there is provided an apparatus for molding the shape of the bottom of a foot, including a flat top plate covering a molding box, having an opening of a predetermined area; a plurality of adjacent bar-like measuring elements supported in an individually vertically movable condition within the box and exposed through the opening; and a thermoplastic film to cover the surface of the opening over the upper ends of the measuring elements.

According to a third aspect of the invention, the apparatus for molding a foot shape includes a heating chamber adjacent to the top plate, for heating the thermoplastic film.

According to a fourth aspect of the invention, there is provided a method of making an insole comprising the steps of supporting a plurality of adjacent bar-like measuring elements in an individually vertically movable condition within an opening of a predetermined area provided in the top plate; covering upper end surfaces of the measuring elements facing the opening with a thermoplastic film which is being plasticized by heating; stepping on the film and the measuring elements thereunder so as to mold the film to the shape of the bottom of the foot and then cooling the film; and cutting the film along the outline of the molded foot shape.

According to the invention as constructed above, when stepping on the film which is plasticized by heating and covers the upper ends surfaces of the measuring elements facing the opening, the measuring elements accompanied with the film are lowered in accordance with the indentation in the sole of the foot and the film is molded to the shape of the bottom of the foot and cooled Thereafter, the lowered measuring elements are lifted up to their original height positions, i.e., the same elevation with the top plate surface, so as to make them ready for another operation.

In the apparatus the preferred embodiment of the invention, the film heating chamber is adjacent to the top plate so that the upper end surfaces of the measuring elements can be covered with the film as soon as it is heated in the heating chamber, namely plasticized, and the apparatus can be integrated, thereby improving the molding efficiency.

Further, an insole that fits the foot is attainable by the mere cutting of the film along the outline of the molded foot shape. This molding apparatus can therefore be used to make insoles and can cut down costs due to its efficiency.

According to the present invention, the foot shape can be molded by stepping on a film plasticized by heating. Further, the invention uses the foot of the person for whose shoes the insoles are intended to mold its shape into the film so that the shape of the foot can be reproduced on the film not only with respect to its length and width and the shapes of toe and heel, but also with respect to the length, width and depth of arch which are very difficult to measure. Thus, very comfortable shoes can be obtained if they are made based on these molded foot shapes Further, according to the apparatus of the preferred embodiment of the invention in which the film heating chamber is provided adjacent to the top plate, the plasticized film can be immediately set over the opening and the apparatus can be integrated, thereby improving the efficiency in molding the foot shapes.

Although insoles have previously been available only as standardized articles, the invention provides a method that enables a simple manufacture of the foot-fitting insoles and, moreover, use of these insoles will greatly decrease fatigue from wearing ill-fitting shoes.

BRIEF DESCRIPTION OF THE DRAWINGS

The preferred embodiment of the present invention will be described with reference to the appended drawings in which.

DETAILED DESCRIPTION OF THE PREFERRED EMBODIMENT

Figure 1:
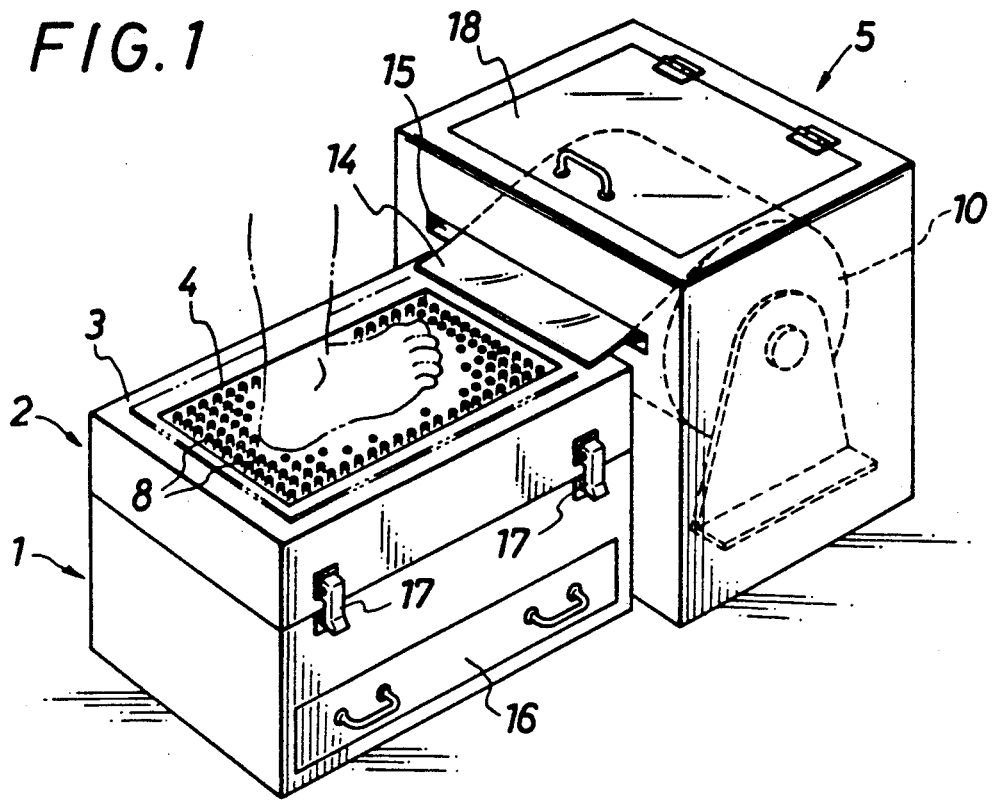
FIG. 1 is a perspective view showing one embodiment of the whole apparatus for molding the shape of a foot according to the present invention.

Referring to FIG. 1, there is shown a square molding box 1, and a cover 2 openably mounted thereto and having a top plate 3 in which an opening of a predetermined area is provided, and a heating chamber 5 adjacent to one end of the box 1.

Figure 2:
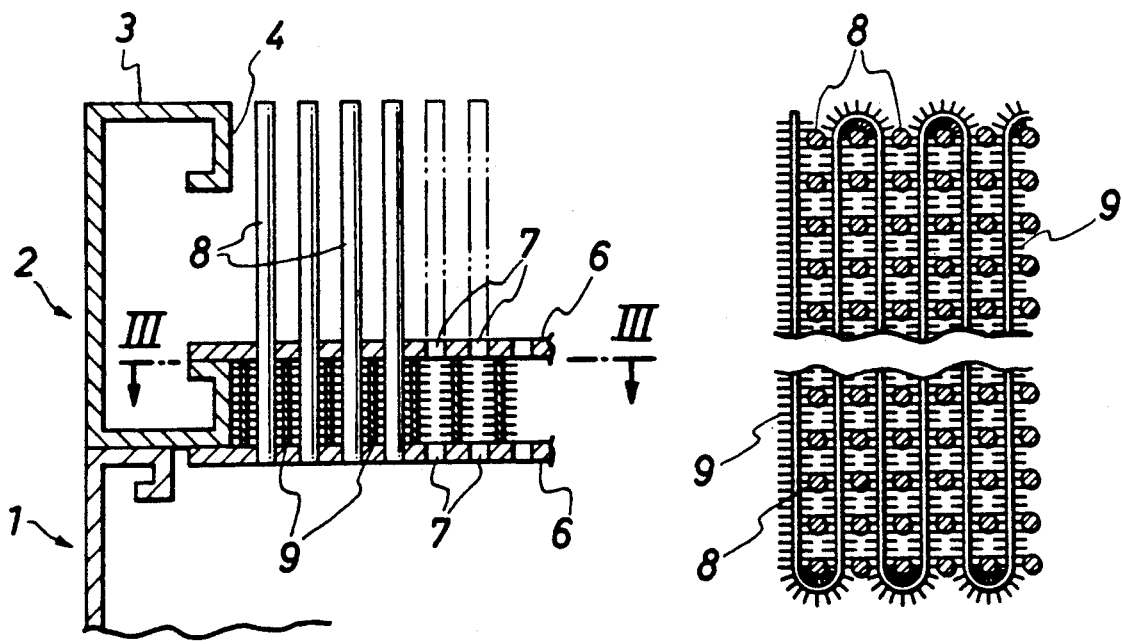
FIG. 2 is a vertical sectional view showing a portion of a top plate.
Figure 3:
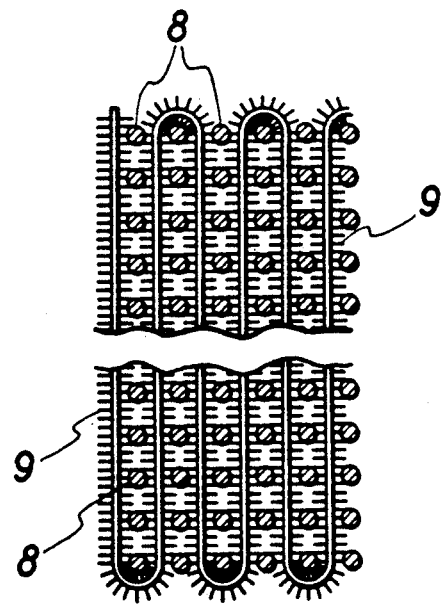
FIG. 3 is a sectional view taken on line III—III of FIG. 2.

Referring to FIG. 2, the cover 2 has therein a pair of fixed, upper and lower, holding plates 6 having a plurality of holes 7 aligned vertically. Bar-like measuring elements 8 are supported in the holes 7 so that they are individually vertically movable, the upper end of each measuring element 8 facing the opening 4. To move the measuring elements 8 up and down individually, a tape napped on both surfaces, such as combined-weave velveteen, is inserted in a space defined by rows of the measuring elements 8 and the upper and lower holding plates 6 to frictionally support the measuring elements, as shown in FIGS. 2 and 3. The mechanism for supporting the measuring elements is not limited to the embodiment shown.

Figure 4:
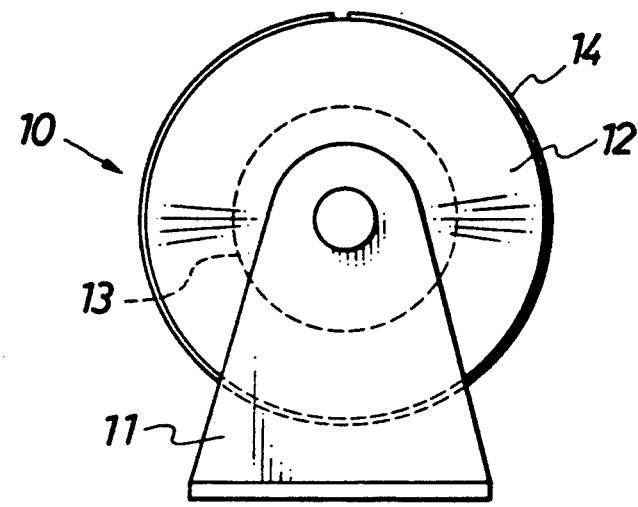
FIG. 4 is a diagrammatic side view of a heating means housed in a heating chamber.
Figure 5:
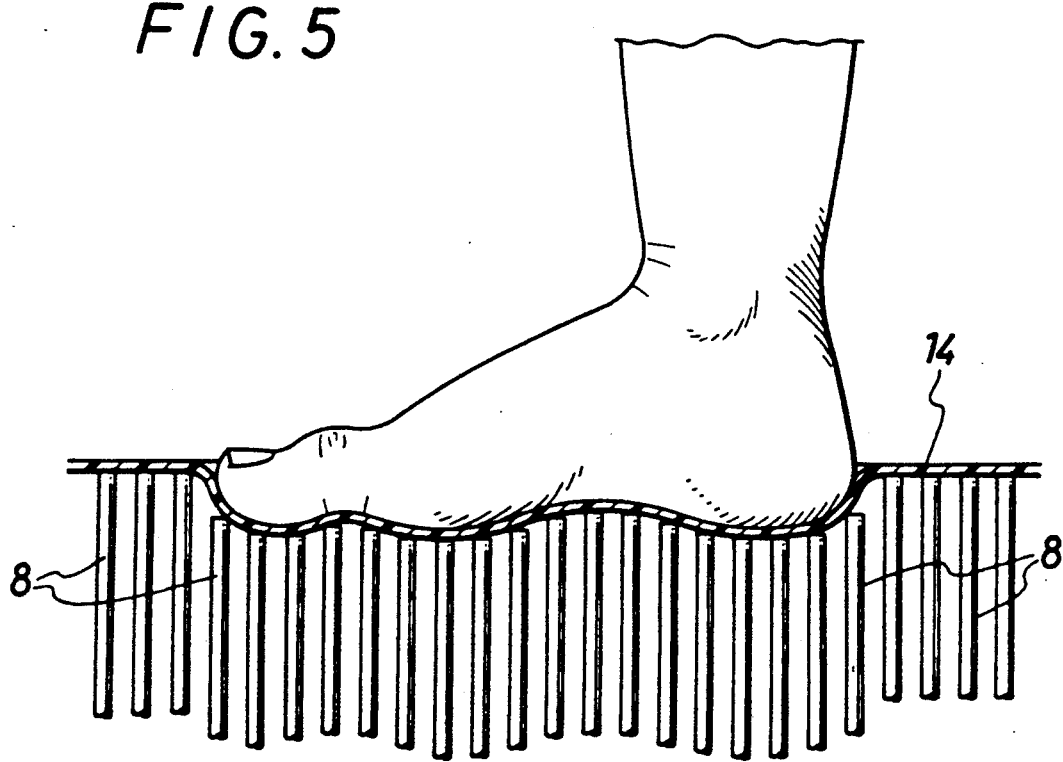
FIG. 5 is a view showing the a film being molded to the shape of the bottom of a foot, according to the invention.

A heating means 10 is housed in the heating chamber 5 and, as shown in FIG. 4, comprises a drum 12 mounted rotatable by a stay 11 within the heating chamber 5, and a heater 13 mounted in the center of the drum 12. When the heater 13 is electrically heated by an order from a conventional control box, not shown, the radiant heat from the heater 13 heats the drum 12 and a film 14 attached therearound which is made of a thermoplastic resin. Referring again to FIG. 1, reference numeral 15 indicates an aperture for pulling out the film 14. A drawer 16 for storing the film 14 is provided at the bottom of the box 1. Locks 17 are provided for the cover 2, and a cover 18 is provided for the heating chamber 5.

In order to mold a foot shape with the above-constructed apparatus, the cover 18 of the heating chamber 5 is opened to mount the film 14 on the drum 12 and a heat switch in the control box is turned on. Thereupon, the control box emits the order for electrically heating with the heater 13, from which radiant heat heats the drum equally and raises the ambient temperature in the heating chamber 5. Consequently, when a certain period of time passes after turning on the heat switch, the film 14 on the drum 12 is heated equably and plasticized.

After the film 14 is sufficiently heated, it is pulled out from the pull-out aperture 15 so as to cover the upper end surfaces of the measuring elements 8 facing the opening 4, whereupon a person places his or her foot on the upper surface of the film to press it down.

Among the measuring elements 8, only those under the film contacting the sole of the foot are lowered while the remaining measuring elements keep their original positions, and thus the lowered measuring elements are pressed down in accordance with the indentation in the sole of the foot. When stepping on the plasticized film 14, the film is pressed between the sole of the foot and the upper end surfaces of the measuring elements 8, whereby the film 14 molds to the shape of the bottom of the foot If it is necessary to heat the film to such a degree that it is hot to the touch of the foot, the film 14 may be covered with a suitable cloth or other suitable material when stepping thereon.

When the film is exposed to the air and lowers in temperature, it loses its plasticity and is hardened to a layer of material molded to the shape of a particular foot. With use of a last formed from, or with the use of, the molded layer of material so obtained, a shoe that fits the foot substantially perfectly can be made.

Figure 6:
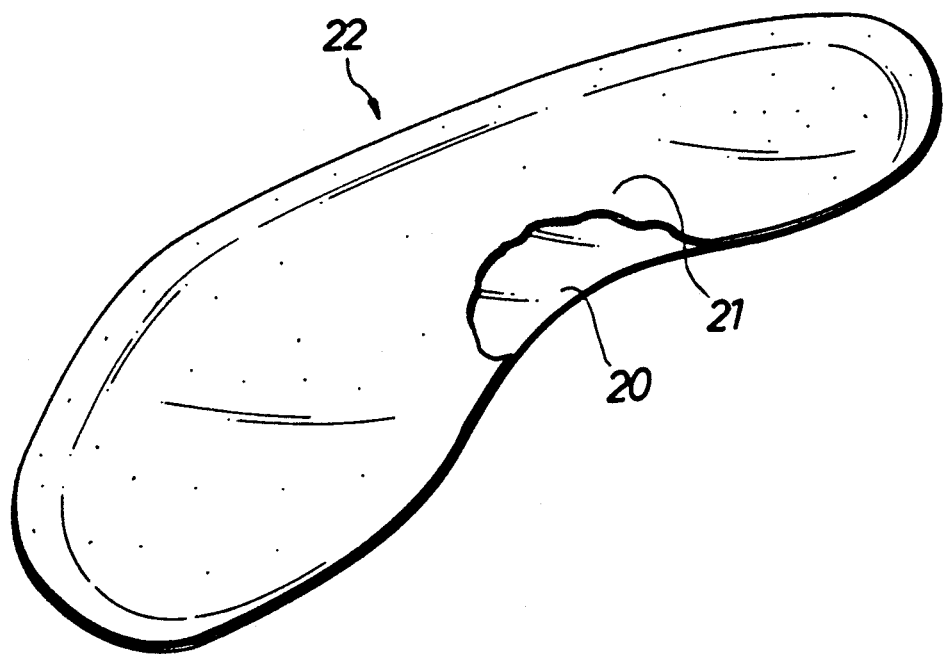
FIG. 6 is a perspective view of an insole made according to the present invention.

By choosing such material for the film that shows a proper elasticity after losing plasticity, the film so molded to a foot shape can be cut along the outline of the foot to make an insole member 20 as shown in FIG. 6. The thus obtained insole member 20 may be lined on its upper surface or both surfaces with a flexible or elastic covering 21 to make an insole 22 which provides sufficient comfort.

Upon completion of the above molding operation, the cover 2 of the box 1 is opened and the measuring elements are lifted up to their original elevation to make them ready for another operation.

In lifting these measuring elements 8, they may be pushed up at their lower ends with a plate, not shown, until they are aligned with the bottom surface of the lower holding plates 6. In case of inserting the two-face napped tape 9 between adjacent rows of the measuring elements 8, as shown in the disclosed embodiment, each measuring element 8 can have necessary and sufficient resistance to ascending and descending movements while retaining its independence, so that it will not be inadvertently accompanied in its movement by the adjacent measuring element 8.

The invention now being fully described, it will be apparent to one of ordinary skill in the art that many changes and modifications can be made thereto without departing from the spirit or scope of the invention as set forth herein.

The present disclosure relates to the subject matter disclosed in Japanese Patent Application No. 62-84430 of Apr. 6th, 1987, the entire specification of which is incorporated herein by reference.

What is claimed is:

1. A method of molding a foot-shaped layer, comprising the steps of:

frictionally supporting a plurality of adjacent bar-like measuring elements in an upper position in an individually vertically movable condition within an opening of a predetermined area provided in a top plate;

heating a thermoplastic film to a plasticized state;

covering upper end surfaces of the measuring elements facing the opening with the thermoplastic film;

stepping with a foot on the film and the measuring elements thereunder with the measuring elements in the upper position and the film in the plasticized state;

during said step of stepping, frictionally resisting downward vertical movement of the measuring elements, so that the measuring elements and portions of the film thereon move downward only by amounts corresponding to the shape of the foot to mold the film to the shape of the foot; and cooling the molded film to obtain the foot-shaped layer.

2. A method as in claim 1, further comprising the step of cutting the foot-shaped layer along the outline of the foot to obtain an insole member.

3. A method of molding a foot-shaped layer, comprising the steps of:

frictionally supporting a plurality of adjacent bar-like measuring elements in an upper position, using a nap disposed on opposite sides of a tape which extends between the measuring elements, the measuring elements being individually vertically movable within an opening provided in a top plate;

heating a thermoplastic film to a plasticized state;

covering upper end surfaces of the measuring elements with the thermoplastic film, the upper end surfaces facing the opening;

stepping with a foot on the film and the measuring elements thereunder, with the measuring elements in the upper position and the film in the plasticized state;

during said step of stepping, frictionally resisting downward vertical movement of the measuring elements with the nap so that the measuring elements and portions of the film thereon move downward only by amounts corresponding to the shape of the foot to mold the film to the shape of the foot; and cooling the molded film to obtain the foot-shaped layer.

4. A method of molding a foot-shaped layer, comprising the steps of:

frictionally supporting a plurality of adjacent bar-like measuring elements in an upper position, the measuring elements being individually vertically movable within an opening provided in a top plate;

heating a thermoplastic film to a plasticized state;

covering upper end surfaces of the measuring elements with the thermoplastic film, the upper end surfaces facing the opening;

stepping with a foot on the film and the measuring elements thereunder, with the measuring elements in the upper position and the film in the plasticized state, so that the individual measuring elements move downward;

continuously during said step of stepping, frictionally resisting the downward vertical movement of the measuring elements so that the measuring elements and portions of the film thereon move downward only by amounts corresponding to the shape of the foot to mold the film to the shape of the foot;

removing the foot from the molded film and the measuring elements;

cooling the molded film to obtain the foot-shaped layer;

removing the foot-shaped layer from the measuring elements; and only after said step of removing the foot, applying a lifting force to the measuring elements against frictional resistance to return the measuring elements to the upper position.

5. A method as in claim 4, wherein a nap disposed on opposite sides of a tape which extends between the measuring elements provides the frictional resistance to vertical movement of the measuring elements during said steps of frictionally supporting the measuring elements in an upper position, frictionally resisting the downward vertical movement of the measuring elements, and applying a lifting force to the measuring elements.

* * * * *